US012465296B2

(12) United States Patent
Kirkham

(10) Patent No.: US 12,465,296 B2
(45) Date of Patent: Nov. 11, 2025

(54) X-RAY SYSTEMS WITH INTERNAL AND EXTERNAL COLLIMATION

(71) Applicant: Varex Imaging Corporation, Salt Lake City, UT (US)

(72) Inventor: Dave Kirkham, South Jordan, UT (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 243 days.

(21) Appl. No.: 18/194,455

(22) Filed: Mar. 31, 2023

(65) Prior Publication Data

US 2024/0065643 A1 Feb. 29, 2024

Related U.S. Application Data

(60) Provisional application No. 63/401,271, filed on Aug. 26, 2022.

(51) Int. Cl.
*A61B 6/02* (2006.01)
*A61B 6/40* (2024.01)

(52) U.S. Cl.
CPC . *A61B 6/02* (2013.01); *A61B 6/40* (2013.01)

(58) Field of Classification Search
CPC ............ A61B 6/40; A61B 6/06; A61B 6/4007
See application file for complete search history.

(56) References Cited

U.S. PATENT DOCUMENTS

| | | | | |
|---|---|---|---|---|
| 9,599,577 | B2 * | 3/2017 | Engel | G21K 1/025 |
| 2008/0267355 | A1 * | 10/2008 | Morton | H01J 35/13 378/124 |
| 2010/0002829 | A1 * | 1/2010 | Dafni | H05G 1/58 378/9 |
| 2010/0020935 | A1 * | 1/2010 | Dafni | H01J 35/04 378/124 |
| 2010/0091938 | A1 * | 4/2010 | Fadler | G21K 1/046 378/150 |
| 2010/0135462 | A1 * | 6/2010 | Harding | G01V 5/00 378/147 |

(Continued)

OTHER PUBLICATIONS

European Appl. No. EP4339968, Partial Search Report dated Feb. 6, 2024 (13 pages).

(Continued)

*Primary Examiner* — David J Makiya
*Assistant Examiner* — Soorena Kefayati
(74) *Attorney, Agent, or Firm* — Dorsey & Whitney LLP

(57) ABSTRACT

Some embodiments include an x-ray system, comprising: a vacuum enclosure; a plurality of electron sources disposed within the vacuum enclosure; an anode including at least one target with a plurality of focal spots disposed in a planar array within the vacuum enclosure, each focal spot configured to generate an x-ray beam in response to an electron beam from a corresponding one of the electron sources; a plurality of first collimators disposed within the vacuum enclosure, each first collimator associated with a corresponding one of the focal spots and configured to collimate the x-ray beam of the corresponding focal spot; and a second collimator integrated with a housing of the vacuum enclosure or external to the vacuum enclosure, the second collimator configured to collimate each of the x-ray beams.

20 Claims, 5 Drawing Sheets

(56) References Cited

U.S. PATENT DOCUMENTS

| | | | | |
|---|---|---|---|---|
| 2011/0075804 | A1* | 3/2011 | Boese | H01J 35/065<br>378/62 |
| 2011/0122992 | A1* | 5/2011 | Hanke | H01J 35/153<br>378/124 |
| 2011/0216884 | A1* | 9/2011 | Tsujii | A61B 6/4405<br>378/62 |
| 2012/0027173 | A1* | 2/2012 | Duerr | H01J 35/065<br>378/62 |
| 2012/0300901 | A1* | 11/2012 | Lewalter | H01J 35/13<br>378/126 |
| 2013/0156157 | A1* | 6/2013 | Engel | G21K 1/025<br>378/62 |
| 2013/0294582 | A1* | 11/2013 | Tsujii | A61B 6/4007<br>378/150 |
| 2015/0078532 | A1* | 3/2015 | Tang | H01J 35/066<br>378/92 |
| 2015/0124934 | A1* | 5/2015 | Gupta | G01N 23/041<br>378/143 |
| 2016/0343533 | A1* | 11/2016 | Morton | G21K 1/02 |
| 2017/0076831 | A1* | 3/2017 | Travish | G21K 1/10 |
| 2017/0162359 | A1* | 6/2017 | Tang | H01J 35/065 |
| 2019/0252148 | A1* | 8/2019 | Travish | A61B 6/56 |
| 2023/0031968 | A1* | 2/2023 | Geithner | H01J 35/065 |

OTHER PUBLICATIONS

European Appl. No. EP4339968, Search Report dated May 24, 2024 (14 pages).

* cited by examiner

X-RAY SYSTEMS WITH INTERNAL AND EXTERNAL COLLIMATION

X-ray tubes used within x-ray systems may include anodes with multiple targets or multiple focal spots on a target. Multiple x-ray beams may be generated from the multiple focal spots on the target or separate targets. The x-ray beams may be collimated to control a field-of-view (FOV) of the x-ray beams.

DETAILED DESCRIPTION

Some embodiments relate to x-ray systems with internal and external collimation. X-ray systems may include multiple x-ray sources. The x-ray beams from the multiple x-ray sources may be directed towards a single location, such as an x-ray detector. As the spacing of the x-ray sources decrease, the x-ray beams begin to overlap closer to the x-ray sources. If the x-ray sources are close enough, the x-ray beams may overlap within a vacuum enclosure. External collimation that may otherwise have been sufficient to collimate each x-ray beam may no longer be possible without differently affecting the field-of-view (FOV) of the x-ray beam on the x-ray detector. Embodiments described herein include both internal and external collimation to allow for control of the FOV even if the x-ray beams overlap within the vacuum enclosure.

Figure 1A:
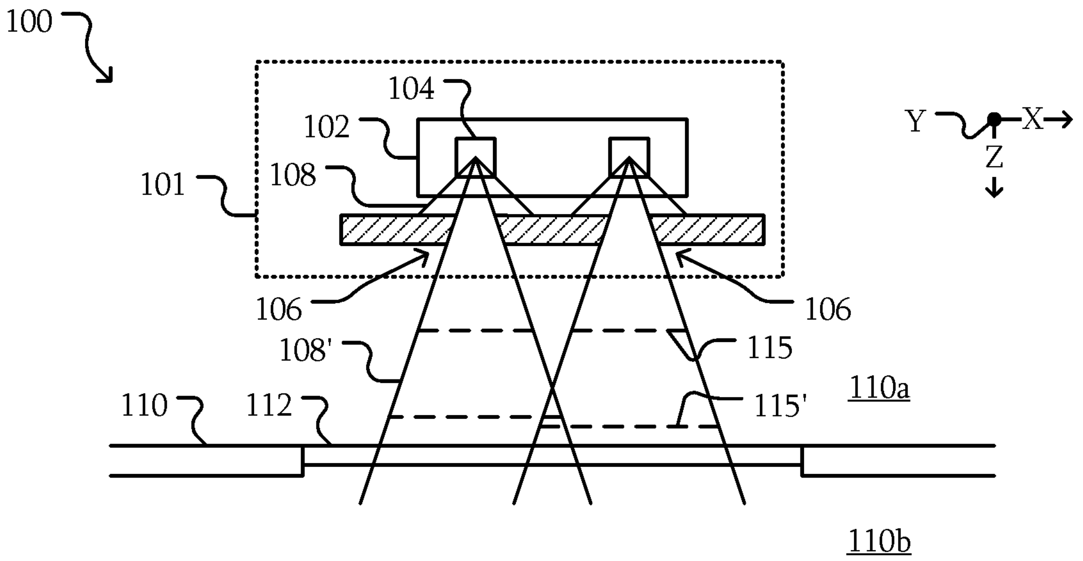
FIGS. 1A-1D are block diagrams of an x-ray system according to some embodiments.
Figure 1B:
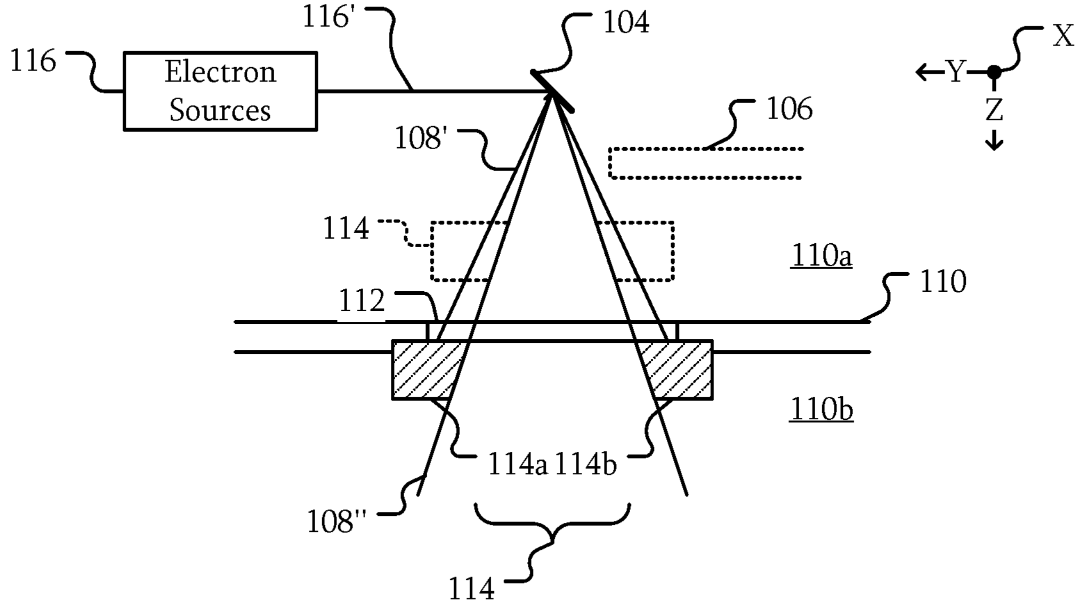
Figure 1C:
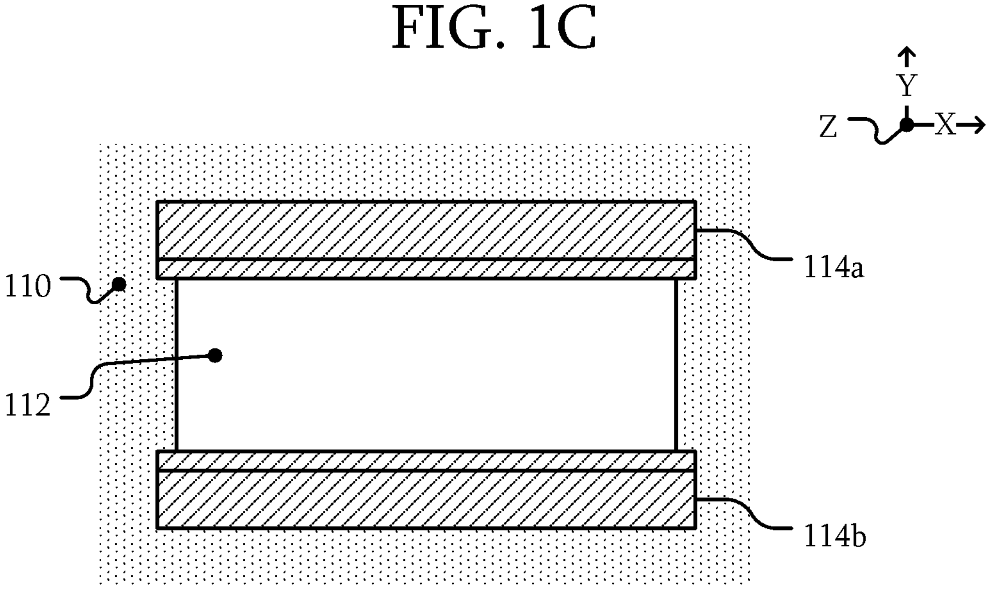

FIGS. 1A-1D are block diagrams of an x-ray system according to some embodiments. Referring to FIGS. 1A-1C, the x-ray system 100 includes an anode 101, multiple first collimators 106, a second collimator 114, multiple electron sources 116, and a vacuum enclosure 110.

The anode 101 is configured to generate multiple x-ray beams 108 in response to incident electrons. The anode 101 includes at least one target 102 with multiple focal spots 104. Each target 102 includes a material such as scandium (Sc), titanium (Ti), cobalt (Co), molybdenum (Mo), rhodium (Rh), palladium (Pd), tungsten (W), platinum (Pt), niobium carbide (NbC or Nb2C), tantalum carbide (TaCx), other x-ray generating materials, or combinations thereof that is configured to generate x-rays in response to incident electrons. In an embodiment, the anode 101 is a linear anode where the anode length (along the X-axis) is 5 times, 10 times, 20, or 50 times the anode width (along the Z-axis), where the length and width correspond to the dimensions of the target side (e.g., in the X-Z plane). In another embodiment, the anode 101 is a curved anode (non-linear) where the anode arc length is 5 times, 10 times, 20, or 50 times the anode arc width, where the arc length and arc width correspond to the dimensions of the target side (e.g., in the X-Z plane). The focal spot 104 is a region or area where the electron beam 116' strikes or hits the target 102. The target 102 can be continuous structure including the material described above with multiple focal spots 104, as illustrated FIG. 1A. In some embodiments, the target 102 is a linear-like target that may be planar and linear or in a curve, such as a continuous curve, a piecewise-linear curve, a combination of such curves, or the like. In an embodiment with a continuous target, the arc length of a curved target (or length of linear target) is 5 times, 10 times, 20, or 50 times the arc width (or width), where the arc length (or length) and arc width (or width) correspond to the dimensions of the side receiving most of the electron beam 116' (e.g., in the X-Z plane). In some embodiments with a piecewise-linear curve or combination of different types of curves may have dimensions similar to the continuous target described above. Alternatively, the target 102 can be multiple discrete target elements, each including the material described above, that may be larger than the associated focal spot 104.

Each of the multiple electron sources 116 is configured to generate an electron beam 116' directed towards a corresponding one of the focal spots 104. An electron source 116 may include a thermionic emitter, a low work function (LWF) emitter, a field emitter, a dispenser cathode, a photo emitter, or the like.

The electron sources 116 and the anode 101, are disposed within the vacuum enclosure 110. The vacuum enclosure 110 is a structure configured to maintain a vacuum in an interior 110*a* separate from the exterior 110*b*. In this example, the electron sources 116 are disposed to emit the electron beams 116' generally in the negative Y direction. The target 102 and the focal spots 104 are disposed to emit x-ray beams 108 generally in the Z direction.

The focal spots 104 are disposed in a planar array. In this example, the focal spots 104 are disposed generally in the X-Z plane. Each of the focal spots 104 may be inclined relative to the Y-Z plane, i.e. rotated about the X axis (as shown in FIG. 1B); however, the focal spots 104 are disposed such that the focal spots 104 are translated from each other and possibly rotated relative to each other, such as in the X-Z plane (e.g., so emitted x-rays can strike the same target object and/or x-ray detector as an example).

Each focal spot 104 is configured to generate x-rays in response to incident electron beams 116' from the electron sources 116. The portion of x-rays directed towards the x-ray window 112 constitute the x-ray beam 108. The x-ray beam 108 may have a particular FOV that widens in the X and Y directions with increasing Z. If the x-ray beam 108 is projected on a two-dimensional (2D) x-ray detector (not illustrated), the x-ray beam 108 FOV may be larger than the x-ray detector area. Thus, portions of the x-ray beam 108 may pass through a patient, object, or the like, but not be detected by the x-ray detector as those x-rays are outside of the area of the x-ray detector. These undetected x-rays result in a larger dose without a corresponding larger image or value to image of the x-ray detector.

To control the FOV of the x-ray beam 108, the x-ray beam 108 may be collimated. The collimation may be performed such that the FOV of the x-ray beam 108 is narrowed to match an area of an x-ray detector. The collimation may be performed by a multi-stage collimation structure. One stage may be configured to collimate the x-ray beam 108 in the X-Z plane, or in the fan angle, while another stage may be configured to collimate the x-ray beam 108 in the Y-Z plane, or in the cone angle.

First collimators 106 are disposed within the vacuum enclosure 110. Each first collimator 106 is associated with a corresponding one of the focal spots 104 and is configured to collimate the x-ray beam 108 of the corresponding focal spot 104. The result is a first collimated x-ray beam 108' associated with each of the focal spots 104. A second collimator 114, illustrated with strips 114*a* and 114*b*, is configured to collimate each of the x-ray beams 108'. That is, the second collimator 114 is downstream from the first collimators 106. Downstream follows the direction of the x-ray beams 108, 108', 108" and/or electron beam 116' and upstream follows the direction opposite of the x-ray beams 108, 108', 108" and/or electron beam 116'.

In some embodiments, the second collimator 114 is integrated with a housing of the vacuum enclosure 110. In other embodiments, the second collimator 114 is external to the vacuum enclosure 110. As illustrated in FIG. 1B, a window 112 is integrated into the vacuum enclosure 110 to maintain the vacuum. In some embodiments, the window 112 is substantially transparent to x-rays, where substantially means less than 2%, 5%, or 20% attenuation of the x-ray beam In about the 90th percentile of all emitted x-rays in terms of energy. For example, the window 112 of an x-ray source operating at 140 kVp will attenuate less than 2%, 5%, or 20% of the x-rays with energies in a particular range, such as between 140 keV and 126 keV. In other embodiments the window 112 may be relatively more transparent, such as having an attenuation of the x-ray beam that is smaller by a factor of 2, 10, or more, than the housing of the vacuum enclosure 110, the second collimator 114, or the like. The second collimator 114 is on the exterior 110*b* of the vacuum enclosure 110. The presence or absence of the second collimator does not affect the integrity of the vacuum enclosure 110. Thus, the second collimator 114 can be external to the vacuum enclosure 110. In examples when second collimator 114 can be external to the vacuum enclosure 110, the second collimator may also use materials that are not vacuum compatible. In some embodiments, the second collimator 114 may be disposed within the vacuum enclosure 110 (as illustrated with dashed lines) but offset and separate from the first collimators 106, where offset means a space between the first collimators 106 and the second collimator 114 in the downstream (in the Z direction).

The first collimators 106 and the second collimator 114 may be formed from a variety of materials. For example, any material with a sufficient thickness (for an x-ray energy) that can stop a sufficient amount of x-rays may be used as part of the first collimators 106 and the second collimator 114. Examples of such materials (collimating material) include lead (Pb), tungsten (W), molybdenum (Mo), stainless steel, or the like. While in some embodiments, the materials of the first collimators 106 and the second collimator 114 may be the same, in other embodiments, the materials of the first collimators 106 may be different from the material of the second collimator 114.

In some embodiments, the first collimators 106 may be disposed close to the anode 101, integrated with the anode 101, and/or at the same potential as the anode 101. The closer the first collimators 106 are to the anode 101 and the focal spots 104, the smaller the first collimators 106 need to be to collimate the x-ray beam 108. As a result, less material is needed, leading to a lighter x-ray system 100. A lighter x-ray system 100 may be more applicable to mobile x-ray systems and may be easier to install. However, a collimator within the vacuum enclosure 110 must be vacuum compatible over the vacuum levels and temperature ranges the x-ray system 100 will experience in operation. Further, it may be more difficult or impractical to change or modify the first collimators 106 after the vacuum has been established in the vacuum enclosure 110.

Figure 1D:
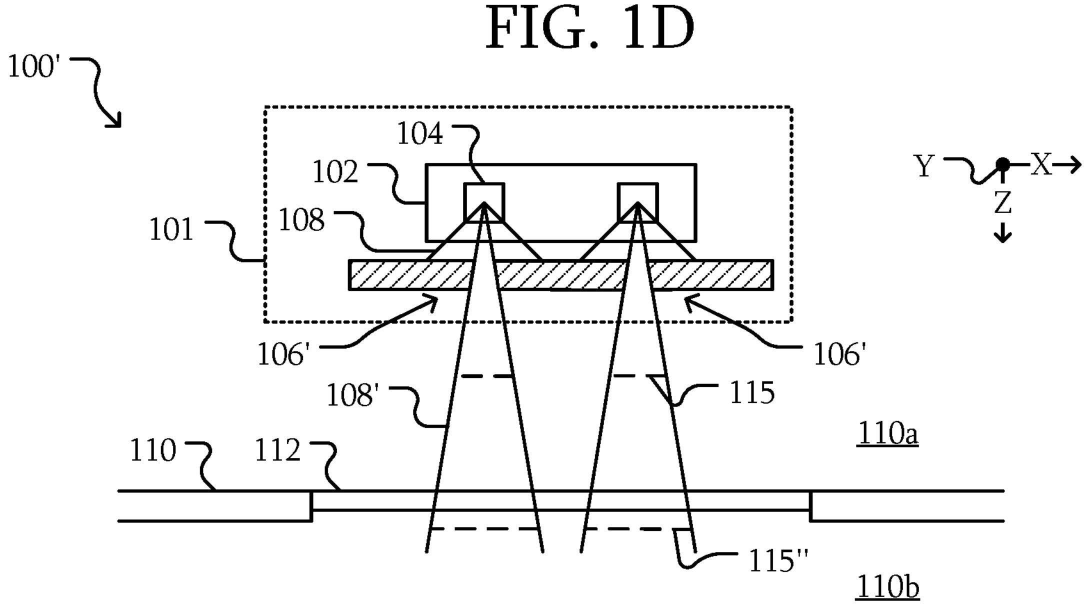

Each of the x-ray beams 108 may need collimation. The collimation may be needed in both the X-Z plane and the Y-Z plane. The first collimators 106 may be configured to collimate in the X-Z plane while the second collimator 114 may be configured to collimate in the Y-Z plane. However, the focal spots 104 and the associated x-ray beams 108 may be disposed relative to each other such that a desired FOV of the x-ray beams 108 after collimation may overlap within the vacuum enclosure 110. The first collimators 106 within the vacuum enclosure 110 allows a desired FOV of the x-ray beams 108 to overlap within the vacuum enclosure 110. In particular, the x-ray beams 108 may have a portion that, after collimation, is the FOV for the associated x-ray beam 108". FOV 115 and FOV 115' represent examples of positions within the vacuum enclosure 110 where the FOVs do not and do overlap, respectively. Here, FOV 115 is representative of the FOV of the associated x-ray beams 108" in the X direction. At the position within the vacuum enclosure 110, the FOV 115 of different x-ray beams 108' do not overlap. However, at the position of FOV 115' within the vacuum enclosure 110, the FOVs 115' overlap. The FOVs 115' are illustrated as being offset slightly in the Z direction to illustrate the overlap. If the portion of the x-ray beams 108 with the desired FOV from different focal spots 104 overlap, one x-ray beam 108 cannot be collimated without affecting the FOV of an adjacent x-ray beam 108. Accordingly, the first collimators 106 are disposed such that each first collimator 106 may be configured to collimate the associated x-ray beam 108 to generate a first collimated x-ray beam 108' without affecting the FOV of an adjacent first collimated x-ray beam 108'. That is, the collimation from the first collimators 106 is performed on the x-ray beam 108 at a position before the FOVs 115 overlap. FIG. 1D illustrates an x-ray system 100' where the FOVs of the x-ray beams 108' do not overlap within the vacuum enclosure 110. The system 100' may be similar to the system 100; however, the first collimators 106' are configured to collimate the x-ray beams 108 such that the FOVs 115" overlap outside of the vacuum enclosure 110. For example, the first collimators 106' may be relatively narrower that the first collimators 106, moving the location of the overlap to be outside of the vacuum enclosure 110. In other embodiments, the position of the focal spots 104 may be separated by a sufficient distance such that even if the first collimators 106' are identical to or wider than the first collimators 106, the FOVs 115" still overlap outside of the vacuum enclosure 110. Other dimensions may be changed to result in the FOVs 115" overlapping outside of the vacuum enclosure 110, such as the distance of the anode 101 to the vacuum enclosure 110.

Referring to FIGS. 1A-C, the first collimated x-ray beams 108' and the associated FOVs may overlap in the X-Z plane within the vacuum enclosure 110. However, as the second collimator 114 may collimate substantially only in the Y-Z plane and not collimate in the X-Z plane, where substantially means that any collimation in the X-Z plane from the second collimator 114 may be due to manufacturing tolerances aligning the first collimators 106 and the second collimator 114, manufacturing tolerances of the second collimator 114, or the like. There may be no additional collimation in the X-Z plane (by the window or other features). The FOV of the first collimated x-ray beams 108' in the X-Z plane remains the same. That is, there may be no further collimation in the X-Z plane after the FOVs overlap. The collimation by the second collimator 106 may be performed after the FOVs overlap as there is no overlap in the Y-Z plane of collimation.

The separation of the collimation into the first collimators 106 and the second collimator 114 has additional benefits. Machining of a collimator that is disposed within the vacuum enclosure 110 may be difficult. In particular, high temperatures materials, such as tungsten and molybdenum, or other materials described above that may be used for the collimator may be difficult to machine with fine detail, especially for collimation in three dimensions (3D), such as in both the X-Z plane and the Y-Z plane. The closer a collimator is to the focal spot 104, the smaller the dimensions of the collimator are to achieve the same FOV.

In addition, the geometry of the collimator may be complex, increasing the difficulty of machining. For example, to machine an opening for a collimator with collimation in both the X-Z and Y-Z planes may require machining a controlled taper in a hole in two axes within a relatively small thickness. In addition, the position and orientation of each individual collimator may vary due to the relative shift in position or rotation of each focal spot 104 and a possibility of the targets being arranged on a non-linear arc. Moreover, the x-ray system 100 may include tens to hundreds of focal spots 104, requiring the machining of tens to hundreds of such complex structures.

However, limiting the specified collimation of the first collimators 106 to collimate in the X-Z plane allows the geometry of the first collimators 106 to be much less complex. Machining in only one direction at a time may be performed to form an opening for the first collimators 106. Some portion of the first collimators 106 may perform collimation in the Y-Z plane as illustrated by the dashed first collimator 106 in FIG. 1B; however, any such collimation may be irrelevant as the collimation of the second collimator 114 may be narrower than any collimation of the first collimators 106. Thus, the collimation in the X-Z plane may be defined by the first collimators 106 and the collimation in the Y-Z plane may be defined by the second collimator 114.

In some embodiments, the second collimator 114 is configured to collimate substantially only within the Y-Z plane that is perpendicular to the X-Z plane of the planar array where substantially means that any collimation in the X-Z plane from the second collimator 114 may be due to manufacturing tolerances aligning the first collimators 106 and the second collimator 114, manufacturing tolerances of the second collimator 114, or the like. In some embodiments, each of the strips 114*a* and 114*b* of the second collimator 114 may extend substantially only parallel to the X-Z plane, the plane of the planar array of the focal spots 104, where substantially parallel means within 2° or 5° of parallel or parallel within manufacturing tolerances of the strips 114*a* and 114*b* and the vacuum enclosure 110. The second collimator 114 may have some thickness in the Y direction to block x-rays; however, the major axis of the strips 114*a* and 114*b* is parallel to the X-Z plane. As illustrated, the strips 114*a* and 114*b* extend substantially only in the X direction, where substantially means within 2° or 5° of the particular direction or within manufacturing tolerances of the strips 114*a* and 114*b* and the vacuum enclosure 110; however as will be described in further detail below, in other embodiments the focal spots 104 and consequently, the strips 114*a* and 114*b* may be disposed along a non-linear arc. That is, the arc of the strips 114*a* and 114*b* may extend substantially only in the X-Z plane, where substantially mean the length (or long dimension) of the strips 114*a* and 114*b* are only in the X-Z plane within manufacturing tolerances of the strips 114*a* and 114*b* and the vacuum enclosure 110.

The strips 114*a* and 114*b* are offset from each other in the Y direction, defining an opening. The opening exposes the window 112 and defines at least part of the FOV of the x-ray beams 108".

In some embodiments, the window 112 of the vacuum enclosure 110 is a continuous window 112 disposed such that each of the x-ray beams 108' passes through the continuous window 112. As the FOVs of the x-ray beams 108' may overlap when the x-ray beams 108' reach the continuous window 112, any obstruction such as a wall, support, or other structure that affects x-rays differently than the window 112 may impact the x-ray beams 108' differently. For example, an obstruction may cause an effect in one position of the FOV of one x-ray beam 108' and cause an effect in a different position of the FOV of another one of the x-ray beams 108'. Accordingly, the window 112 may be continuous such that no obstructions appear in the window 112.

In some embodiments, the second collimator 114 is disposed downstream from the window 112. The second collimator 114 may be disposed directly on the window 112. In other embodiments, the second collimator 114 may be offset from the window 112 further downstream from the window 112.

As described above, in some embodiments, the FOVs of x-ray beams 108' may overlap within the vacuum enclosure 110. In particular, the FOV of at least one of the x-ray beams 108' overlaps with the FOV of another one of the x-ray beams 108' within the vacuum enclosure 110 after being collimated by the first collimators 106. However, in other embodiments, the FOVs of the x-ray beams 108' may overlap outside of the vacuum enclosure 110.

In some embodiments, the second collimator 114 may provide structural support for the window 112. The window 112 may be formed from a stable, light weight material with a low atomic number and is compatible in vacuum up to about 400 C. For example, the window 112 may be formed from a material such as aluminum (Al), titanium (Ti), beryllium (Be), high density carbon (C, like diamond or graphite), or copper (Cu). In addition, the window 112 and/or the housing of the vacuum enclosure 110 adjacent to the window 112 may be relatively thin. Thus, the window may be a relatively thin structure susceptible to flexing, warping, or other distortion. This susceptibility of such thin structures may be exacerbated when the window 112 is a continuous window 112. Additional structural support may be provided by the second collimator 114. The second collimator 114 may extend along a perimeter of the window 112. In some embodiments, the second collimator 114 may be attached to both the window 112 and the vacuum enclosure 110. In addition, the second collimator 114 may include additional material or thickness relative to the window 112 or vacuum enclosure 110. In some embodiments, the second collimator 114 is not directly attached to the window 112, but is attached to the vacuum enclosure 110 near the window 112 such that the second collimator 114 still provides structural support to the window 112 indirectly through the vacuum enclosure 110.

Figure 2:
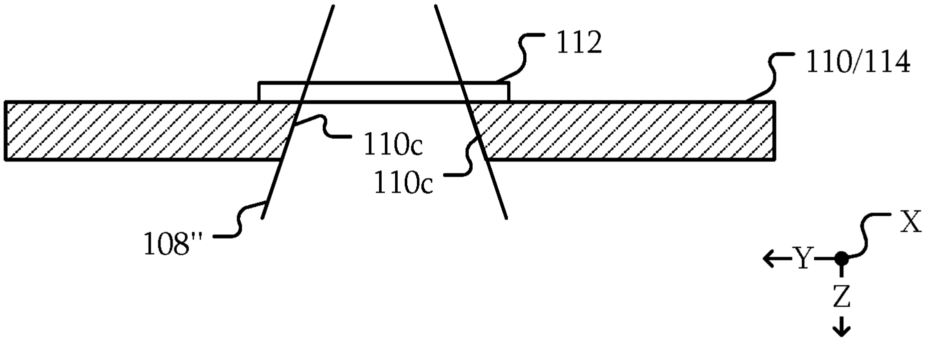
FIG. 2 is a block diagram an x-ray window and collimator of an x-ray system according to some embodiments.

FIG. 2 is a block diagram an x-ray window and collimator of an x-ray system according to some embodiments. Although only a vacuum enclosure 110, window 112, and second collimator 114 are illustrated, the structure may be used in the x-ray system 100 of FIG. 1. In some embodiments, the second collimator 114 is integrated with the housing of the vacuum enclosure 110. This is illustrated with the combined 110/114 reference numbers. For example, the housing of the vacuum enclosure 110 may be formed of stainless steel. A sufficient amount of stainless steel may be provided adjacent to the window 112 and extending a sufficient distance from the window 112 in the Y direction to sufficiently collimate the x-ray beams 108'.

In some embodiments, the edges 110*c* of the vacuum enclosure 110 adjacent to the window 112 that extends in the X direction may have a slope. The slope may be defined by the desired collimation in the Y-Z plane to form the second collimated x-ray beam 108".

Figure 3A:
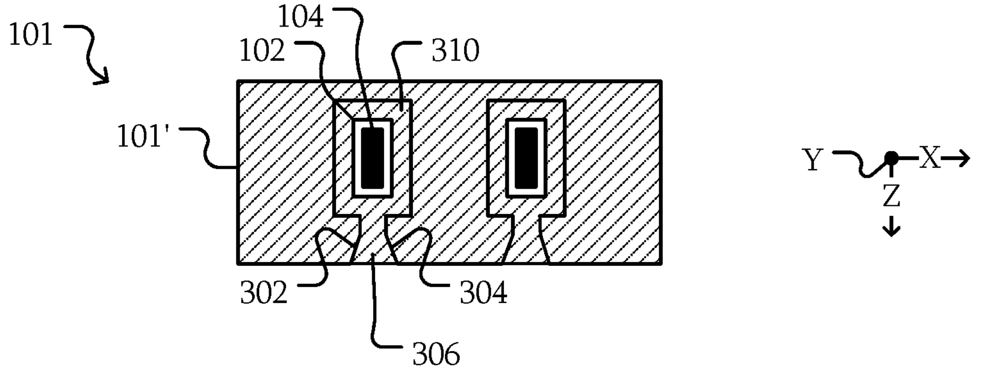
FIGS. 3A-C are various views of an anode of an x-ray tube according to some embodiments.
Figure 3B:
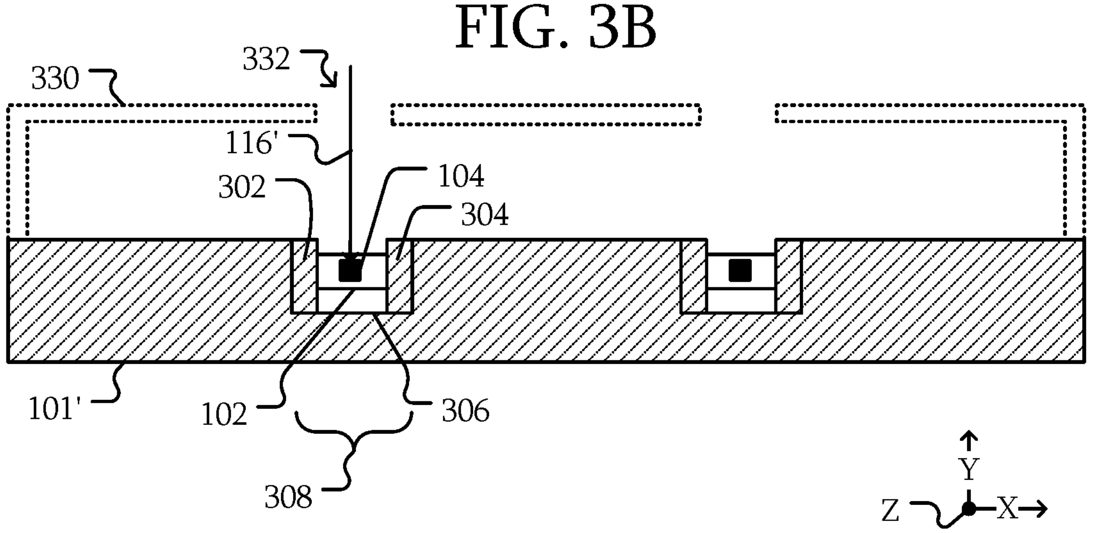
Figure 3C:
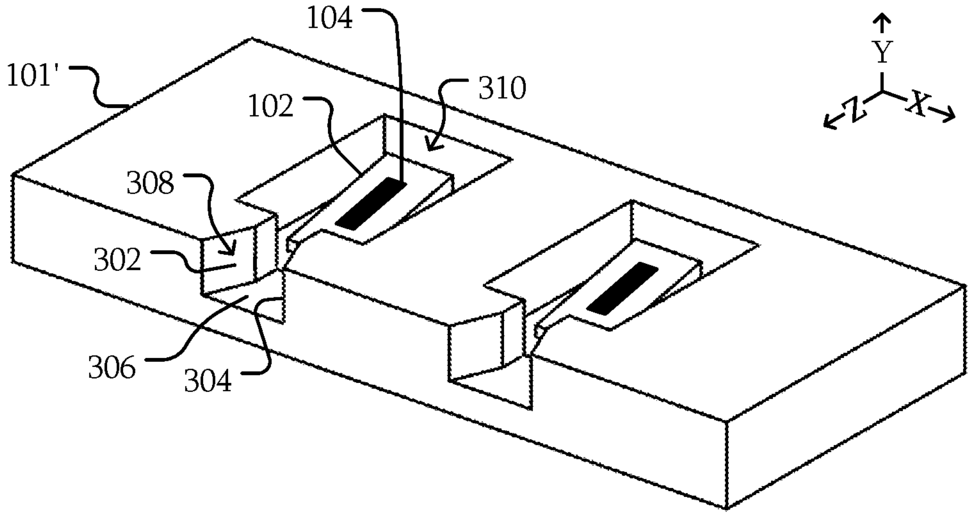

FIGS. 3A-C are various views of an anode of an x-ray tube according to some embodiments. FIG. 3A is a top view in the negative Y direction. FIG. 3B is a side view in the negative Z direction. FIG. 3C is an isometric view. In some embodiments, the first collimators 106 may be integrated with the anode 101. For example, the anode 101 may include a continuous strip 101' of collimating material. Each of the first collimators 106 is formed in the continuous strip 101'. Accordingly, when manufacturing the anode 101, a block of collimating material may be machined into a desired shape to integrate the first collimators 106 with the anode 101.

In some embodiments, each first collimator 106 includes multiple surfaces. A first surface 306 is substantially parallel to the X-Z plane of the planar array of the focal spots 104. Each of a second surface 302 and a third surface 304 of each first collimator 106 is substantially perpendicular to the first surface 306, where substantially perpendicular means between 88° and 92°, 85° and 95°, or 80° and 90° of the first surface 306 or perpendicular within manufacturing tolerances of the anode 101. The second surface 302 and third surface 304 of each first collimator 106 may form surfaces that perform the collimation of the x-ray beams 108 to form the first collimated x-ray beams 108'.

In some embodiments, the second surface 302 and third surface 304 of each first collimator 106 can define the FOVs of the x-ray beams 108' and whether the overlap of the FOVs of adjacent x-ray beams 108' occurs within the vacuum enclosure 110 or outside the vacuum enclosure 110 after being collimated by the first collimators 106. For example, when the plane formed by the second surface 302 of a first collimator 106 intersects downstream with the plane formed by the third surface 304 of an adjacent first collimator 106 before the window 112 (as showed in FIG. 1A) for any adjacent first collimators 106, then a FOV of at least one of the x-ray beams 108' overlaps with a FOV of another one of the x-ray beams 108' within the vacuum enclosure 110 after being collimated by the first collimators 106. The overlap of the FOV of an x-ray beam 108' with the FOV of another x-ray beam 108' can be determined by the geometry and spacing of the first collimator 106 relative to the window 112 without activating the x-ray system 100 and the electron sources 116. In an example, when the plane formed by the second surface 302 of a first collimator 106 intersects downstream with the plane formed by the third surface 304 of an adjacent first collimator 106 after the window 112 (as showed in FIG. 1A) for every adjacent first collimators 106, then a FOV of at least one of the x-ray beams 108' does not overlap with a FOV of another one of the x-ray beams within the vacuum enclosure after being collimated by the first collimators. In other embodiments, the overlap of the FOVs of the x-ray beams 108' may depend on the width of the focal spots 104, the width of the target 102.

In some embodiments, the first surface 306, the second surface 302, and the third surface 304 form a channel 308 that is open towards a direction towards the electron sources 116. For example, as illustrated in FIG. 3B, the Y direction may point towards the electron sources 116. Thus, the channel 308 may be open to the Y direction.

The channel 308 may simplify the machining of the continuous strip 101'. For example, the focal spots 104 may be disposed in openings 310 in the continuous strip 101'. The openings 310 may be open to the Y direction so that the openings 310 permit the electron beams 116' from the electron sources 116 to reach the focal spots 104. Machining of the channel 308 and the opening 310 may be part of the same operation. The channel 308 and the opening 310 may be contiguous.

Moreover, a simpler machining process may result in the perpendicular surfaces 302 and 304 described above. A bit of a computer numerical control (CNC) machine may be translated in the X-Z plane to machine out both the channel 308 and the opening 310.

Although the first collimators 106 have been described as being integrated with the anode 101 in one example, the first collimators 106 may be integrated with the anode 101 in other ways. For example, the first collimators 106 may be integrated with a shroud 330 that is also configured to contain backscatter electrons. The shroud 330 may extend over the anode 101 and between the focal spots 104 and the electron sources 116. The shroud may include openings 332 through which the electron beams 116' pass.

Although an anode 101 that is formed from substantially all collimating material has been used as an example, the first collimators 106 may be integrated with the anode 101 in other ways, where substantially all means 90%, 95%, or 98% collimating material. For example, the first collimators 106 may be formed in a continuous strip 101' that is mounted on a substrate. The focal spots 104 may be separately mounted on that substrate.

Although the first surface 306 has been described as being parallel to the X-Z plane as an example, in other embodiments, the first surface 306 may not be parallel to X-Z plane. However, the first surface 306 may still be perpendicular to the second surface 302 and third surface 304.

Figure 4:
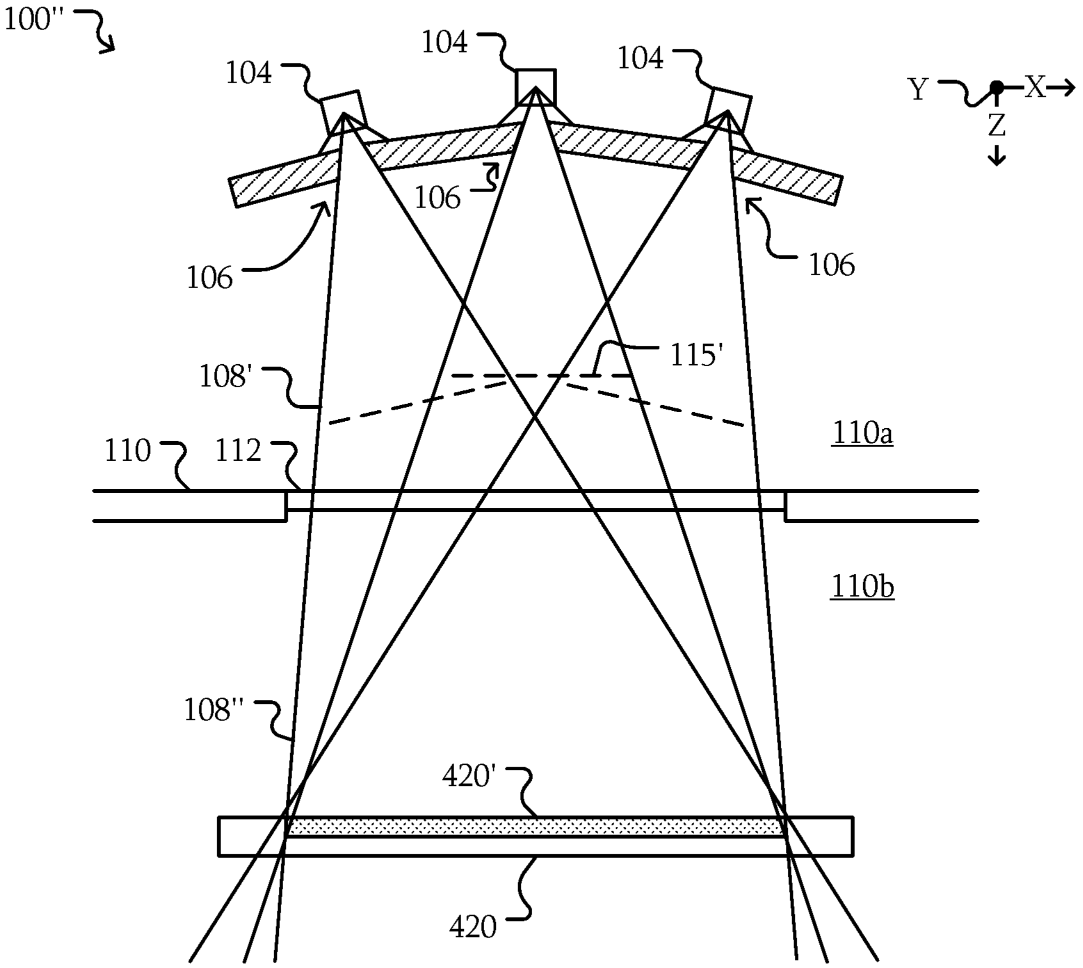
FIG. 4 is a block diagram of an x-ray system with a non-linear anode according to some embodiments.

FIG. 4 is a block diagram of an x-ray system with a non-linear anode according to some embodiments. The x-ray system 100" may be similar to the x-ray system 100 described above including the various structures illustrated in FIGS. 1A-C. However, the focal spots 104 are disposed along a non-linear arc. The focal spots 104 may still be disposed substantially in the X-Z plane as the arc may be substantially parallel to the X-Z plane. However, the focal spots 104 may be offset both in the X direction and the Z direction from each other. In addition, the focal spots 104 may be rotated relative to each other about the Y direction. The first collimators 106 may be similarly translated and potentially rotated to correspond to the associated focal spots 104 to collimate the x-ray beams 108 into the x-ray beams 108'. The FOVs 115' in the X-Z plane overlap within the vacuum enclosure 110 similar to the system 100 described above.

In some embodiments, the x-ray system 100" includes an x-ray detector 420. The x-ray detector 420 includes a detector area 420' configured to detect incident x-rays 108". The FOV of each of the x-ray beams 108" after collimation by the second collimator 114 and the corresponding first collimator 106 is substantially coincident with a detector area 420' of the x-ray detector 420, where substantially coincident means an overlap of the x-ray beam 108" and the detector area 420' is greater than or equal to 80%, 90%, 95%, or 98%. The preferred position of the x-ray detector 420 may be established in the X direction and the Z direction by the collimation of the first collimators 106. The position of the x-ray detector 420 may be established in the Y direction based on the second collimator 114 similar to that of FIG. 1B.

Figure 5:
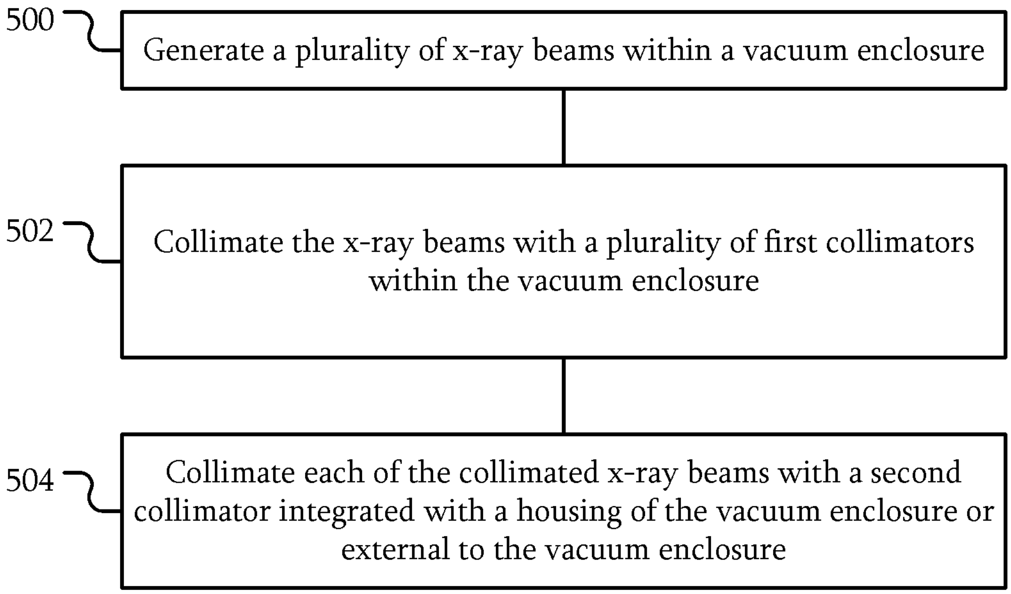
FIG. 5 is a flowchart of an operation of an x-ray system according to some embodiments.

FIG. 5 is a flowchart of an operation of an x-ray system according to some embodiments. The x-ray system 100 of FIGS. 1A-C will be used as an example; however, the operation may be performed using other x-ray systems such as the x-ray system 100" or the like.

In 500, multiple x-ray beams 108 are generated within a vacuum enclosure 110. For example, the electron sources 116 may generated multiple electron beams 116' directed towards focal spots 104 of a target 102. In response to the electron beams 116' the focal spots 104 may generate multiple x-ray beams 108.

In 502, the x-ray beams 108 are collimated with first collimators 106 within the vacuum enclosure 110. In some embodiments, the x-ray beams 108 are collimated such that a FOV of at least one of the collimated x-ray beams 108' overlaps with a FOV of another of the collimated x-ray beams 108' within the vacuum enclosure 110. In 504, each of the collimated x-ray beams 108' is collimated with a second collimator 114 integrated with a housing of the vacuum enclosure 110 or external to the vacuum enclosure 110.

Figure 6:
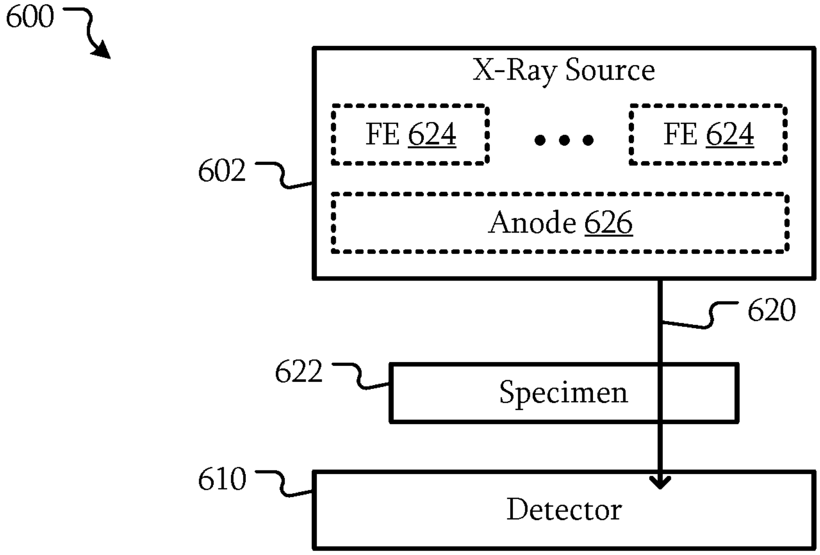
FIG. 6 is a block diagram of an x-ray imaging system according to some embodiments.

FIG. 6 is a block diagram of an x-ray imaging system according to some embodiments. The x-ray imaging system 600 includes an x-ray source 602 and detector 610. The x-ray source 602 may include an x-ray system 100 or the like as described above. In some embodiments, the x-ray source 602 includes multiple field emitters (FE) 624. Electron beams from the field emitters 624 may be directed towards an anode 626 to generate x-rays 620. The x-ray source 602 is disposed relative to the detector 610 such that x-rays 620 may be generated to pass through a specimen 622 and detected by the detector 610. In some embodiments, the detector 610 is part of a medical imaging system. In other embodiments, the x-ray imaging system 600 may include a portable vehicle scanning system as part of a cargo scanning system. The system 600 may be any system that may include an x-ray detector.

Some embodiments include an x-ray system, comprising: a vacuum enclosure 110; a plurality of electron sources 116 disposed within the vacuum enclosure 110; an anode 101 including at least one target 102 with a plurality of focal spots 104 disposed in a planar array within the vacuum enclosure 110, each focal spot 104 configured to generate an x-ray beam in response to an electron beam from a corresponding one of the electron sources 116; a plurality of first collimators 106 disposed within the vacuum enclosure 110, each first collimator 106 associated with a corresponding one of the focal spots 104 and configured to collimate the x-ray beam of the corresponding focal spot 104; and a second collimator 114 integrated with a housing of the vacuum enclosure 110 or external to the vacuum enclosure 110, the second collimator 114 configured to collimate each of the x-ray beams.

In some embodiments, the second collimator 114 is configured to collimate substantially only within a first plane substantially perpendicular to a plane of the planar array.

In some embodiments, a field of view (FOV) of at least one of the x-ray beams overlaps with a FOV of another one of the x-ray beams within the vacuum enclosure 110 after being collimated by the first collimators 106.

In some embodiments, the second collimator 114 is integrated with the housing of the vacuum enclosure 110.

In some embodiments, the second collimator 114 is external to the vacuum enclosure 110.

In some embodiments, the second collimator 114 comprises a first strip **114*a* and a second strip 114*b*; the first strip 114*a* is offset from the second strip 114*b*, defining an opening; each of the first strip 114*a* and the second strip 114*b***: includes a material configured to perform the collimation; and is substantially parallel to a plane of the planar array.

In some embodiments, the vacuum enclosure 110 comprises a continuous window 112 disposed such that each of the x-ray beams passes through the continuous window 112.

In some embodiments, the second collimator 114 is disposed downstream from the continuous window 112.

In some embodiments, the second collimator 114 is configured to support the continuous window 112.

In some embodiments, the first collimators 106 are integrated with the anode 101.

In some embodiments, the anode 101 includes a continuous strip 101' of collimating material; and each of the first collimators 106 is formed in the continuous strip 101'.

In some embodiments, the continuous strip 101' comprises, for each x-ray beam: a first surface 306 substantially parallel to a plane of the planar array; a second surface 302 substantially perpendicular to the first surface 306; and a third surface 304 substantially perpendicular to the first surface 306. The third surface 304 may face the second surface 302.

In some embodiments, the first surface 206, the second surface 302, and the third surface 304 form a channel 308 that is open towards a direction towards the electron sources 116.

In some embodiments, the at least one target 102 comprises a plurality of targets 102, each target 102 corresponding to one of the focal spots 104; the anode 101 includes a plurality of openings, each opening corresponding to one of the targets 102 and the corresponding focal spot 104 and configured to admit the electron beam to the focal spot 104 from the corresponding one of the electron sources 116; and each of the channels is contiguous with a corresponding opening of the anode 101.

In some embodiments, the focal spots 104 of the at least one target 102 are disposed along a non-linear arc.

In some embodiments, the x-ray system further comprises an x-ray detector; wherein a field of view of a majority of the x-ray beams after collimation by the second collimator 114 and the corresponding first collimator 106 is substantially coincident with a detector area of the x-ray detector. The majority of the x-ray beams may include each x-ray beam in some embodiments.

In some embodiments, the x-ray system further comprises a shroud 330 disposed between the electron sources 116 and the anode 101.

Some embodiments include a method, comprising: generating a plurality of x-ray beams within a vacuum enclosure 110; collimating the x-ray beams with a plurality of first collimators 106 within the vacuum enclosure 110; and collimating each of the collimated x-ray beams with a second collimator 114 integrated with a housing of the vacuum enclosure 110 or external to the vacuum enclosure 110.

In some embodiments, collimating the x-ray beams with the first collimators 106 within the vacuum enclosure 110 comprises collimating the x-ray beams with the first collimators 106 within the vacuum enclosure 110 such that at least one field of view (FOV) of the collimated x-ray beams overlaps with a FOV of another of the collimated x-ray beams within the vacuum enclosure 110.

Some embodiments include an x-ray system, comprising: a vacuum enclosure 110; a plurality of electron sources 116 disposed within the vacuum enclosure 110; an anode 101 including a plurality of targets 102 disposed in a planar array within the vacuum enclosure 110, each target 102 configured to generate an x-ray beam in response to an electron beam from a corresponding one of the electron sources 116; a plurality of first collimators 106 disposed within the vacuum enclosure 110, each first collimator 106 associated with a corresponding one of the targets 102 and configured to collimate the x-ray beam of the corresponding target 102; and a second collimator 114 disposed within the vacuum enclosure 110 and offset from the first collimators 106, the second collimator 114 configured to collimate each of the x-ray beams.

In some embodiments, the x-ray system further comprises a third collimator 114 integrated with a housing of the vacuum enclosure 110 or external to the vacuum enclosure 110, the third collimator configured to collimate each of the x-ray beams. The third collimator 114 may be similar to the second collimators 114 described above that are either integrated with a housing of the vacuum enclosure 110 or external to the vacuum enclosure 110.

Some embodiments include an x-ray system, comprising: means for generating a plurality of x-ray beams within a vacuum enclosure; means for collimating each of the x-ray beams within the vacuum enclosure; and means for collimating each of the x-ray beams at or external to the vacuum enclosure.

Examples of the means for generating a plurality of x-ray beams within a vacuum enclosure include the electron sources 116, the anode 101, the target 102, the focal spots 104, or the like. Examples of the means for collimating each of the x-ray beams within the vacuum include the first collimators 106 or the like.

Examples of the means for collimating each of the x-ray beams at or external to the vacuum enclosure include the second collimators 114.

In some embodiments, the means for collimating each of the x-ray beams within the vacuum enclosure further comprises: means for collimating each of the x-ray beams such that a field of view (FOV) at least one of the collimated x-ray beams overlaps with a FOV of another of the collimated x-ray beams within the vacuum enclosure. Examples of the means for collimating each of the x-ray beams such that a field of view (FOV) at least one of the collimated x-ray beams overlaps with a FOV of another of the collimated x-ray beams within the vacuum enclosure include the first collimators 106 or the like.

Although the structures, devices, methods, and systems have been described in accordance with particular embodiments, one of ordinary skill in the art will readily recognize that many variations to the particular embodiments are possible, and any variations should therefore be considered to be within the spirit and scope disclosed herein. Accordingly, many modifications may be made by one of ordinary skill in the art without departing from the spirit and scope of the appended claims.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the claims beginning with claim [x] and ending with the claim that immediately precedes this one," where the bracketed term "[x]" is replaced with the number of the most recently recited independent claim. For example, for the first claim set that begins with independent claim 1, claim 4 can depend from either of claims 1 and 3, with these separate dependencies yielding two distinct embodiments; claim 5 can depend from any one of claim 1, 3, or 4, with these separate dependencies yielding three distinct embodiments; claim 6 can depend from any one of claim 1, 3, 4, or 5, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed to cover the corresponding structure, material, or acts described herein and equivalents thereof in accordance with 35 U.S.C. § 112(f). Embodiments of the invention in which an exclusive property or privilege is claimed are defined as follows.

The invention claimed is:

1. An x-ray system, comprising:
- a vacuum enclosure;
- a plurality of electron sources disposed within the vacuum enclosure;
- an anode including at least one target with a plurality of focal spots disposed in a planar array in an X-Z plane within the vacuum enclosure, each of the plurality of focal spots configured to generate an x-ray beam in response to an electron beam from a corresponding one of the plurality of electron sources;
- a plurality of first collimators disposed within the vacuum enclosure, each of the plurality of first collimators being associated with a corresponding one of the plurality of focal spots and configured to collimate the x-ray beam of the corresponding one of the plurality of focal spots; and
- a second collimator integrated with a housing of the vacuum enclosure or external to the vacuum enclosure, the second collimator configured to collimate each of the x-ray beams substantially only in a Y-Z plane perpendicular to the X-Z plane.

2. The x-ray system of claim 1, wherein:
- a field of view (FOV) of at least one of the x-ray beams overlaps with a FOV of another one of the x-ray beams within the vacuum enclosure after being collimated by the plurality of first collimators.

3. The x-ray system of claim 1, wherein:
- the second collimator is integrated with the housing of the vacuum enclosure.

4. The x-ray system of claim 1, wherein:
- the second collimator is external to the vacuum enclosure.

5. The x-ray system of claim 1, wherein:
- the second collimator comprises a first strip and a second strip;
- the first strip is offset from the second strip, defining an opening; and
- each of the first strip and the second strip:
  - includes a material configured to perform the collimation; and
  - is substantially parallel to a plane of the planar array.

6. The x-ray system of claim 1, wherein:
- the vacuum enclosure comprises a continuous window disposed such that each of the x-ray beams passes through the continuous window.

7. The x-ray system of claim 1, wherein:

the plurality of first collimators is are integrated with the anode.

8. The x-ray system of claim 1, wherein:

the anode includes a continuous strip of collimating material; and each of the plurality of first collimators is formed in the continuous strip.

9. The x-ray system of claim 1, wherein:

the plurality of focal spots of the at least one target are disposed along a non-linear arc.

10. The x-ray system of claim 1, further comprising:

an x-ray detector;

wherein a field of view of a majority of the x-ray beams after collimation by the second collimator and the corresponding one of the plurality of first collimators is substantially coincident with a detector area of the x-ray detector.

11. The x-ray system of claim 1, further comprising:

a shroud disposed between the plurality of electron sources and the anode.

12. The x-ray system of claim 6, wherein:

the second collimator is disposed downstream from the continuous window.

13. The x-ray system of claim 6, wherein:

the second collimator is configured to support the continuous window.

14. The x-ray system of claim 8, wherein the continuous strip comprises, for each x-ray beam:

a first surface substantially parallel to a plane of the planar array;

a second surface substantially perpendicular to the first surface; and a third surface substantially perpendicular to the first.

15. The x-ray system of claim 14, wherein:

the first surface, the second surface, and the third surface form a channel that is open towards a direction towards the plurality of electron sources.

16. The x-ray system of claim 15, wherein:

the at least one target comprises a plurality of targets, each of the plurality of targets corresponding to one of the plurality of focal spots;

the anode includes a plurality of openings, each of the plurality of openings corresponding to one of the plurality of targets and the corresponding one of the plurality of focal spots and configured to admit the electron beam to the focal spot from the corresponding one of the plurality of electron sources; and each of the channels is contiguous with a corresponding one of the plurality of openings of the anode.

17. A method, comprising:

generating a plurality of x-ray beams within a vacuum enclosure;

collimating the plurality of x-ray beams with a plurality of first collimators within the vacuum enclosure; and collimating each of the plurality of collimated x-ray beams with a second collimator integrated with a housing of the vacuum enclosure or external to the vacuum enclosure, wherein:

the plurality of first collimators collimates the plurality of x-ray beams substantially in an X-Z plane;

the second collimator comprises a plurality of strips, each strip extending substantially parallel to the X-Z plane; and the second collimator collimates the plurality of collimated x-ray beams substantially in a Y-Z plane perpendicular to the X-Z plane.

18. The method of claim 17, wherein:

collimating the plurality of x-ray beams with the plurality of first collimators within the vacuum enclosure comprises collimating the plurality of x-ray beams with the plurality of first collimators within the vacuum enclosure such that at least one field of view (FOV) of the plurality of collimated x-ray beams overlaps with a FOV of another of the plurality of collimated x-ray beams within the vacuum enclosure.

19. An x-ray system, comprising:

electron sources and an anode for generating a plurality of x-ray beams within a vacuum enclosure;

first collimators for collimating each of the plurality of x-ray beams within the vacuum enclosure, each of the first collimators comprising:

- a first collimating surface;
- a second collimating surface opposite the first collimating surface; and
- a third surface extending between the first collimating surface and the second collimating surface, wherein the first collimating surface, the second collimating surface, and the third surface form a channel that is open opposite the third surface, wherein target surfaces of the anode and the first collimators are formed from a continuous material; and a second collimator for collimating each of the plurality of x-ray beams at or external to the vacuum enclosure.

20. The x-ray system of claim 19, wherein the first collimators further collimate each of the plurality of x-ray beams such that a field of view (FOV) of at least one of the plurality of collimated x-ray beams overlaps with a FOV of another of the plurality of collimated x-ray beams within the vacuum enclosure.

* * * * *